United States Patent [19]

Berthold et al.

[11] Patent Number: 5,517,851
[45] Date of Patent: May 21, 1996

[54] METHOD AND APPARATUS FOR PREDICTING ONSET OF INTERGRANULAR ATTACK AND STRESS CORROSION CRACKING IN TUBING SUBJECTED TO HOSTILE ENVIRONMENT

[75] Inventors: John W. Berthold, Salem, Ohio; Thomas O. Passell, Palo Alto, Calif.; Garry W. Roman, Alliance, Ohio

[73] Assignee: Electric Power Research Institute, Palo Alto, Calif.

[21] Appl. No.: 366,216

[22] Filed: Dec. 29, 1994

[51] Int. Cl.$^6$ .................................................. G08B 21/00
[52] U.S. Cl. .................................................. 73/87; 73/86
[58] Field of Search .................................. 73/86, 87, 760, 73/800, 865.6, 866.4; 976/DIG. 139, DIG. 207; 324/71.2; 385/13

[56] References Cited

U.S. PATENT DOCUMENTS

| | | | |
|---|---|---|---|
| 3,104,355 | 9/1963 | Holmes et al. | 73/86 |
| 3,352,149 | 11/1967 | Sherlock et al. | 324/71.2 |
| 3,846,795 | 11/1974 | Jones | 73/86 |
| 4,468,613 | 8/1984 | Slaugh et al. | 324/71.2 |
| 4,915,473 | 4/1990 | Haese et al. | 73/800 |
| 5,020,379 | 6/1991 | Berthold et al. | 73/800 |
| 5,178,822 | 1/1993 | Buford III et al. | 73/86 |
| 5,361,284 | 11/1994 | Baum et al. | 73/86 |

*Primary Examiner*—Richard Chilcot
*Assistant Examiner*—Ronald Biegel
*Attorney, Agent, or Firm*—Flehr, Hohbach, Test, Albritton & Herbert; Michael A. Kaufman

[57] ABSTRACT

An autoclave-enclosed sidestream model boiler is used to predict the onset of intergranular attack ("IGA") and stress corrosion cracking ("SCC") within tubing associated with a power generator. Power generator final feed water is fluid coupled to a pipe within the model boiler, which pipe is strain-gage monitored, preferably using welded fiber optic strain gage devices. The monitored pipe includes a crevice region that produces a water-starved region in which chemical impurities in the feed water become concentrated. A cylindrical heater, located within a portion of the monitored pipe, promotes the water-starved region. A cylindrical portion of the pipe wall preferably is thinned, generally in the region bounding the crevice. Thinning promotes the onset of IGA/SCC within the monitored pipe and also passively amplifies the effects of IGA/SCC to promote easier strain detection. To further promote stress, the monitored pipe is subjected to loading and unloading from an axial load. Drift in the strain gage measurement can be substantially eliminated by taking measurements under axial load and no load conditions, as these two conditions may be attained within a short time of each other, e.g., a few minutes. Long term monitoring of the strain gages provides a measure of onset and progression of IGA and SCC within the autoclave model. These measurements can provide a prediction of the onset of IGA and SCC within the actual power generator, allowing corrective action to be taken before a pipe fails.

20 Claims, 6 Drawing Sheets

METHOD AND APPARATUS FOR PREDICTING ONSET OF INTERGRANULAR ATTACK AND STRESS CORROSION CRACKING IN TUBING SUBJECTED TO HOSTILE ENVIRONMENT

FIELD OF THE INVENTION

The present invention relates generally to strain measurement at elevated temperature, and more specifically to methods and apparatuses for predicting onset of inergranular attack and stress corrosion cracking within tubing subjected to elevated temperature (e.g., >600° F.) and other hostile environment.

BACKGROUND OF THE INVENTION

Fossil fuel powered steam generators, nuclear powered steam systems, and the like, employ many thousands of pipes through which water flows at high temperature and high pressure. The water within the pipe may flow at perhaps 1 m$^3$/second, at 600° F. or more, and at pressures of perhaps 1,100 psi. In a nuclear steam system, the outer surface of the pipe may be exposed to liquid at perhaps 2,500 psi. To help stabilize these pipes against vibrations, the pipes are routed through pipe-sized openings in support plates. Unfortunately, the interfaces between these openings and the pipe creates thousands of potential crevices, whose presence can promote pipe cracking.

As used herein, the term "crevice" denotes a water starved region in which heat transfer occurs so rapidly that input water does not arrive sufficiently rapidly to replace water already in the crevice ration that is boiled away. The flowing water is normally non-corrosive, but contains chemical impurities that become concentrated in the crevice as the water boils away. In the water flow-starved boiling region within the crevice, a highly aggressive corrosive brine is created that, unfortunately, can attack, corrode and eventually causes cracks to occur within the pipe wall.

As a result of the corrosion, high temperature and flow pressures, strain within the pipe wall occurs under stress. Cracks, typically forming from the outer wall inward, can result that reduce the strength of the pipe cross-section. Unless detected sufficiently early, pipe failure and costly steam generator down-time can result. The failure mechanism appears to result from progressive intergranular attack and stress corrosion cracking, or "IGA/SCC".

Unfortunately, it is difficult to reliably measure or successfully predict IGA/SCC failure on a long term basis within the hostile environment typified by the steam generators. For example, it is known in the art to monitor strain at high temperatures using non-contact strain measuring techniques. But these devices are poorly suited for long-term measurements on power generation components, whose surfaces are often insulated and/or are subject to degradation. In addition, the pipes to be monitored are frequently located in regions where visual interrogation is difficult or impossible. Further, noncontact strain measurement devices are affected by temperature, opacity, and the turbulence of any intervening atmosphere.

Contact strain gages such as electrical resistance gages are also known in the art. Such devices have long been used to sense strain at temperatures exceeding 700° F. on a long-term basis, and at even higher temperatures for short-term or dynamic measurements. For example, bonded resistance gages are commonly used continuously at temperatures up to 500° F. and have relatively high compliance, e.g., the ability to readily conform to the surface of the object under measurement.

So-called "Eaton" and "Kyowa" weldable resistance gages are also useable at such temperatures, but have less compliance due to package stiffness. In the 600° F. to 650° F. range, such gages are made with a modified nickelchrome alloy that has good drift characteristics, relative small apparent strain, and repeatable apparent strain characteristics. As used herein, "drift" refers to the stability of the strain gage output, while "apparent strain" refers to the change in output of the strain gage as a function of temperature in a regime in which hysteresis effects do not predominate. It is difficult to adequately temperature compensate such devices using heat treatment techniques. Above 650° F., the sense material undergoes a metallurgical phase transition that can "reset" the temperature compensation, causing radical zero shifts.

In the 1000° F. to 1100° F. range, it is difficult to retain calibration, especially with resistance strain gages. Apparent strain, drift, and hystersis due to temperature cycling present problems. At present, it is not known how to accomplish long-term static strain measurement at such elevated temperatures.

The drift problem has been somewhat addressed in the prior art using high-temperature capacitive strain gages. However, such devices are not generally suitable for dynamic measurements above 100 Hz. Although low drift characteristics enable capacitive strain gages to measure creep strain change at steady-state, installation, calibration and other documentation is costly. Nonetheless, capacitive type gages represent the only presently available contact devices useable for field measurement of creep strain at temperatures above 1000° F.

All of the above-described gages suffer the common problem of requiring electrical connections, which frequently are difficult to implement in a power plant generator environment. By contrast, fiber optic strain gages do not require such connections, and are useable at temperatures exceeding 700° F.

A microbend fiber optic type strain gage is described in U.S. Pat. No. 5,020,379 to Berthold, in which a strain sensing optical fiber is sandwiched between a pair of tooth-edged end plates. When the end plates move toward or away from each other, the fiber is deformed, amplitude modulating a light signal transmitted through the fiber. This modulation is detected to provide strain information having excellent resolution. A second, reference, optical fiber is sandwiched between a similar pair of tooth-edged end plates that are locked to each other but not attached to the structure. Both fibers are equal in length and are routed in parallel. As such, the reference fiber compensates for source brightness variations and changes in fiber transmission over time, thus providing temperature compensation.

As such, the Berthold device is similar to a conventional strain gage in that it modulates the "resistance" to light passing through the sensing fiber. The device is also similar to a conventional capacitance gage in that it relies upon relative movement of two plates for its measurement. However, unlike the capacitance gage, the microbend fiber stiffness makes the gage less compliant than capacitance gages, but still more compliant than weldable resistance gages. The microbend fiber optic strain gage can provide stable and extended life data at temperatures up to 1100° F.

In short, although a variety of strain gages are known in the prior art, there remains a need for a mechanism by which the onset and progression of IGA/SCC can be predicted on a long term basis in the hostile environment that typifies power generation plants.

The present invention provides a method and apparatus for providing such predictions.

SUMMARY OF THE INVENTION

The present invention comprises an autoclave-enclosed sidestream model boiler that is used to predict the onset of intergranular attack ("IGA") and stress corrosion cracking ("SCC") within tubing associated with a power generator. Final feed water from the power generator is fluid coupled to a pipe within the model boiler, which pipe is strain-gage monitored, preferably using welded fiber optic strain gage devices.

The monitored pipe includes a crevice region that produces a water-starved region in which chemical impurities in the feed water become concentrated. To promote the water-starved region, a cylindrical heater is located within a portion of the monitored pipe. A cylindrical portion of the pipe wall preferably is thinned, generally in the region bounding the crevice. Thinning promotes the onset of IGA/SCC within the monitored pipe and also passively amplifies the effects of IGA/SCC to promote easier strain detection. To further promote stress, the monitored pipe is subjected to controllable loading and unloading from an axial load. Drift in the strain gage measurement can be substantially eliminated by taking measurements under axial load and no load conditions, as these two conditions may be attained within a short time of each other, e.g., a few minutes.

Thus, within the autoclave, the present invention replicates within the crevice in the monitored pipe the water chemistry present in the pipes in the power generator. Long term monitoring of the strain gages provides a measure sure of onset and progression of IGA and SCC within the autoclave model. These measurements can provide a prediction of the onset of IGA and SCC within the actual power generator, allowing corrective action to be taken before a pipe fails.

Other features and advantages of the invention will appear from the following description in which the preferred embodiments have been set forth in detail, in conjunction with the accompanying drawings.

DETAILED DESCRIPTION OF THE PREFERRED EMBODIMENT

Figure 1:
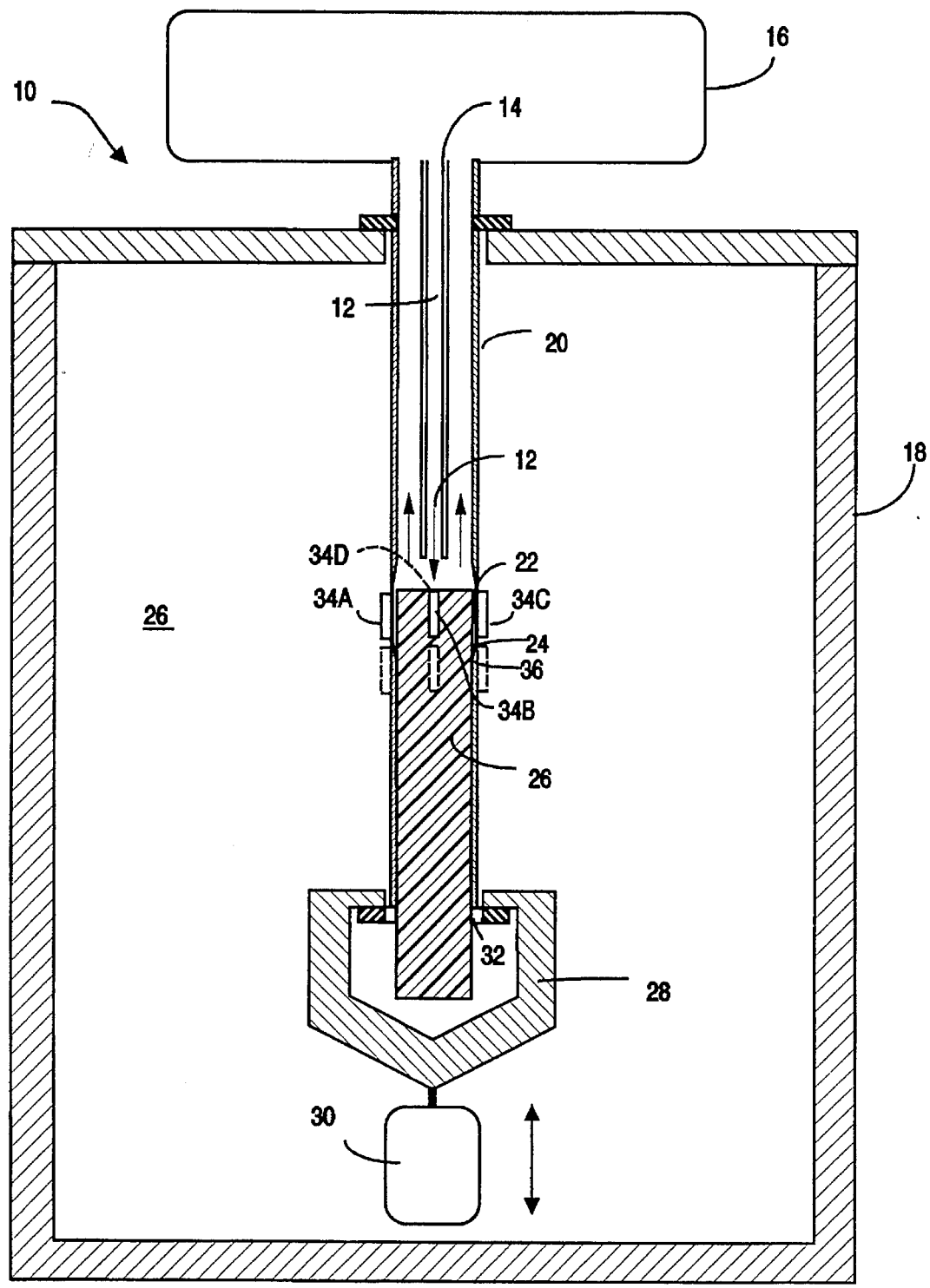
FIG. 1 is a cross-sectional depiction of an apparatus for predicting onset and progression of IGA and SCC in a power plant, according to the present invention.

As shown by FIG. 1, the present invention 10 is fluid-coupled to receive final feed water 12, via a pipe 14, from a power plant generator, shown generically as 16. Plant 16 may be, by way of example, be a steam plant or a nuclear power plant. Although flow rate within the pipes associated with generator 16 may be 1 m$^3$/second or so, flow rate through pipe 14 will typically be scaled down to range from perhaps 30 cc/minute to about 50 cc/minute, although other flow rates may be used.

Within an autoclave 18, pipe 14 is coaxially surrounded by pipe 20, preferably made from the same material, or materially somewhat less corrosion-resistant, as the pipes within generator 16. Autoclave 18 is about 6" (15.24 cm) in diameter by perhaps 12"(30.48 cm) in length, and can establish a bounded super-heated pressurized steam region for the present invention. In practice, in nuclear steam systems, the secondary tubes within plant 16 may be operated with large external and internal pressures. In fossil fueled generators, the external pressure is ambient, and thus autoclave 18 is operated at ambient pressure for convenience. In any event, however, autoclave 18 provides a measure of safety, protecting personnel in the event pipe 20 ruptures due to cracking or the like, and due to the high internal pipe pressure.

Typically the pipes within generator 16 and pipe 20 are Inconel alloy 600 material. In the preferred embodiment, pipe 20 is about 0.750" (1.905 cm) outer diameter, has a nominal wall thickness of 0,043" (1.09 mm) and is about 6" (15.24 cm) in length.

In the preferred embodiment, a portion 22 of the wall of pipe 20 is thinned to about 0.030" (0.762 mm), to make this wall portion weaker and thus more sensitive to stress-induced cracks, and also to form a crevice region 24. Of course a crevice region 24 could be fabricated other than by thinning the wall of pipe 20. For example, a radially inwardly projecting member could instead be formed on the inner wall of pipe 20 adjacent the desired crevice region, or the desired crevice region could be "filled" with a porous plug or deposit of iron oxide, so-called corrosion product material.

It is appreciated that the function of the crevice 24 is to produce a water-starved region in which heat transfer occurs sufficiently rapidly that input water (from generator 16) does not arrive rapidly enough to replace water already in the crevice region that is boiled away. To ensure such a water-starved region 24, a cylindrical heater element 26 is provided within pipe 20, whose distal end extends at least beyond region 24. Heater 26 typically will be in the hundred watt to thousand watt range. The outer shell of heater element 26 preferably is a piece of Inconel alloy 718 tube.

To help minimize corrosion on the outer surface of tube 20, a helium or argon cover gas (shown as 26) may be present within autoclave 18. The internal pressure of this gas, or of the autoclave itself, may be up to about 1000 psi, although in the preferred embodiment the autoclave is not pressurized.

Applicants have found that IGA/SCC of tube 20 may advantageously be accelerated by the application of an axial load 28, preferably movable vertically (as indicated by the double arrow) by a hydraulic cylinder mechanism 30. As such, mechanism 30 can cause weight 28 to put tube 20 into a loaded state (e.g., in which a dead weight 28 exerts a precisely controlled downward force), or into an unloaded state (in which weight 28 essentially is not present). As shown in FIG. 1, a pressure seal 32 preferably is provided at the lower end of tube 20 near the interface with the load 28.

In the preferred embodiment, load 28 is about 615 pounds (280 Kg). In the presence of an internal pressure of about 1100 psi within pipe 20, heater 26 caused boiling to occur in crevice region 24 at a target temperature of about 550° F. In a loaded state, axial dead weight 28 and the internal pressure put tube 20 into a bi-axial stress state. By bi-axial, it is meant that tube 20 underwent both hoop stress and axial stress, similar to what would be experienced by an actual steam generator tube within generator 16.

Four preferably microbend fiber optic strain gage assemblies 34A, 34B, 34C and 34D were mounted equidistant on the periphery of the external surface of the thinned region 22 of tube 20. By equidistant it is meant that when viewed from the top of tube 20, these gages are located at 0°, 90°, 180° and 270°. Of course fewer or more than four strain gages may be used and they may be placed in other locations, and gages other than fiber optic devices may be used. As noted, crevice 24 concentrates aggressive components from the fluid 12 such that intergranular attack and stress-corrosion cracking in the pipe wall is aggressively encouraged.

Output signals from the strain gages are monitored to track changes in strain in the wall of tube 20, as an indication of IGA/SCC progression in tube 20, and thus as a prediction of IGA/SCC progression in tubes in plant generator 16. Interestingly, IGA/SCC cracks were discovered to begin not in the thin wall section 22 as was anticipated, but rather in the region shown as 36 in FIG. 1, defined generally by the interface of the exterior vertical surface of heater 26 and the portion of the inner wall of tube 20 as the inner wall begins to thin.

Possibly this region defines a second crevice. In view of these findings, future embodiments will include at least one strain gage assembly located on the exterior surface of pipe 20 adjacent region 36 in the region(s) denoted by phantom outline.

Figure 2:
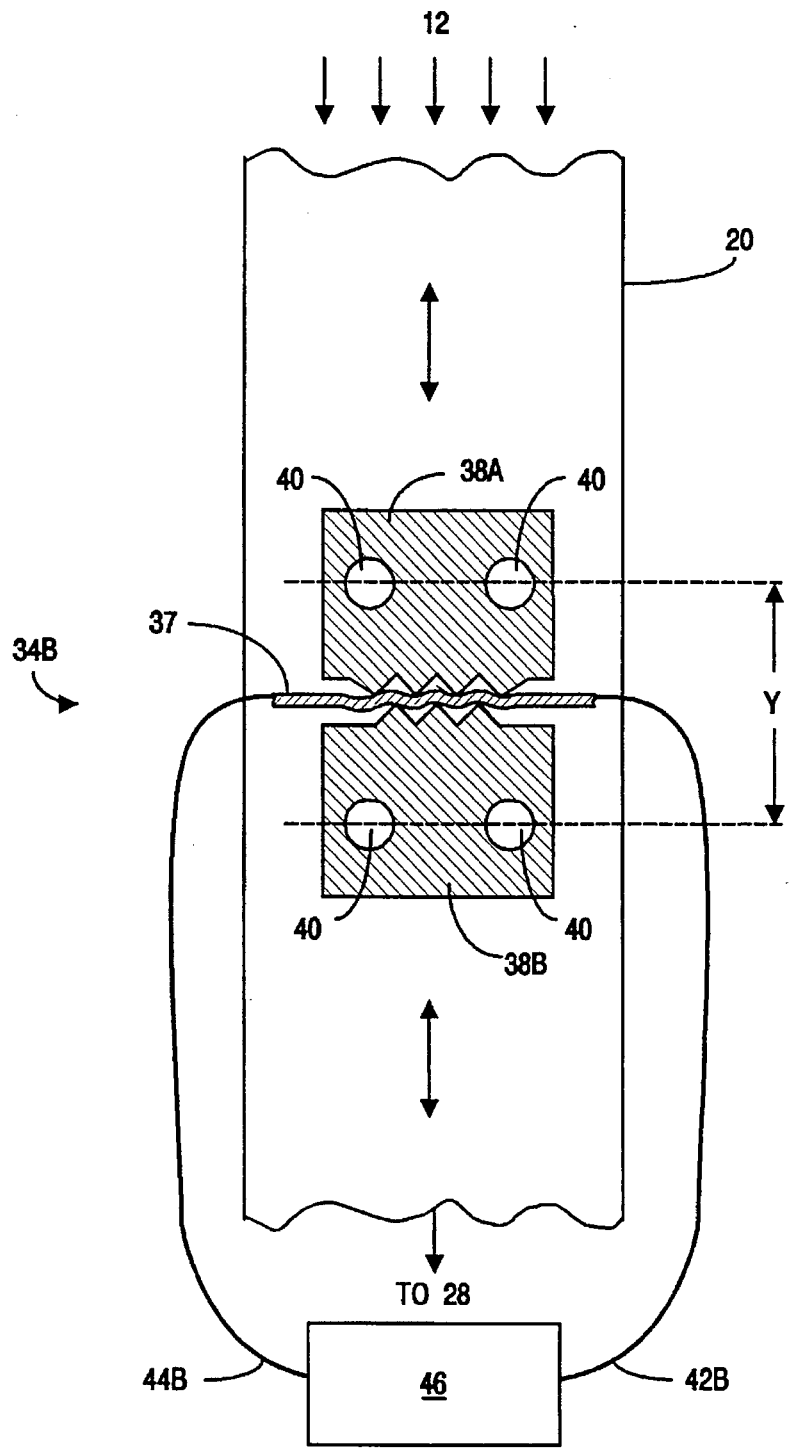
FIG. 2 is a plan view of a fiber optic microbend strain gage assembly, as used in the present invention.

As shown in FIG. 2, a typical strain gage assembly 34B includes a fiber optic element 37 disposed between first and second tooth-edged end plates 38A, 38B that are spot welded at locations 40 to the outer surface of pipe 20. The vertical distance Y between the spot welds defines the active gage length for assembly 34B, typically a distance of about 0.30" (7.62 mm). In the preferred embodiment, fiber 37 was a length of Polymicro FHP100140170 material, with ST-type optical connectors on each end.

In the preferred embodiment, end plates 38A, 38B were machined from Inconel alloy 600 tube, having 0.88" (2.23 cm) outer diameter and 0.050" (0.127 cm) wall thickness, and the toothed-portion of the plates had a 1.5 mm pitch. The spotwelds on a plate were spaced-apart 20.8° center-to-center, were 0.060" (1.52 mm) in diameter, and 0.040 " 1.01 mm) deep. Of course, other plate configurations may be used, and as noted, assembly 34B may use conventional strain gages rather than fiber optic devices.

The first, input, end of fiber optic 37 is optically coupled via lead 42B to a light source within instrumentation 46, while the second, output, end of the fiber optic 37 is coupled via a lead 44B to instrumentation 44 (to be described later with respect to FIG. 3).

As indicated in FIG. 2 by the double arrows, as the plates 38A, 38B move toward or away from each other, e.g., due to IGA/SCC associated with pipe 20, fiber 37 is deformed by the toothed portion of the plates. The light from source 42 that is transmitted through the fiber is amplitude modulated by the deformation. Demodulation of the fiber optic output light signalby instrumentation 46 produces information as to the strain in pipe 20. This information is then used to predict onset and progression of IGA/SCC within pipes in plant generator 16.

In use, longterm monitoring of strain measurements for onset and progression of IGA/SCC is desired. However, as noted, prior art strain measuring devices are prone to drift, which would impair the ability to discern onset or progression of IGA/SCC. Thus, in the present invention, mechanism 30 is periodically activated, e.g., once per day, to temporarily unload weight 28 from tube 20. Weight 28 provides a highly accurate and repeatable axial load, and mechanism 30 can unload and load weight 28 from tube 20 within a minute or so. This permits absolutely attaining repeatable strain gage output readings for load and unload condition, wherein drift plays no significant role due to the very short interval between load and unload measurements.

In practice, as IGA/SCC proceeds, the wall of tube 20 will lose load carrying capacity, essentially because the effective wall cross-section is diminished by cracks. Thus, when mechanism 30 unloads weight 28, a steady increase in the change in the output from the strain gages (e.g., 34A) is observed. The relative change in strain per unit of weight 28 will tend to track the loss of load carrying capacity of the tube wall. This, in turn, can provide a direct indication of the progression of the IGA/SCC within tube 20, and by implication within tubes found in plant generator 16. Because loading and unloading weight 28 from tube 20 can eliminate drift in the strain measurements, the present invention can provide on a longterm monitoring basis a direct correlation between such measurements and the load carrying capacity of tube 20, and by implication tubes within generator 16.

Figure 3:
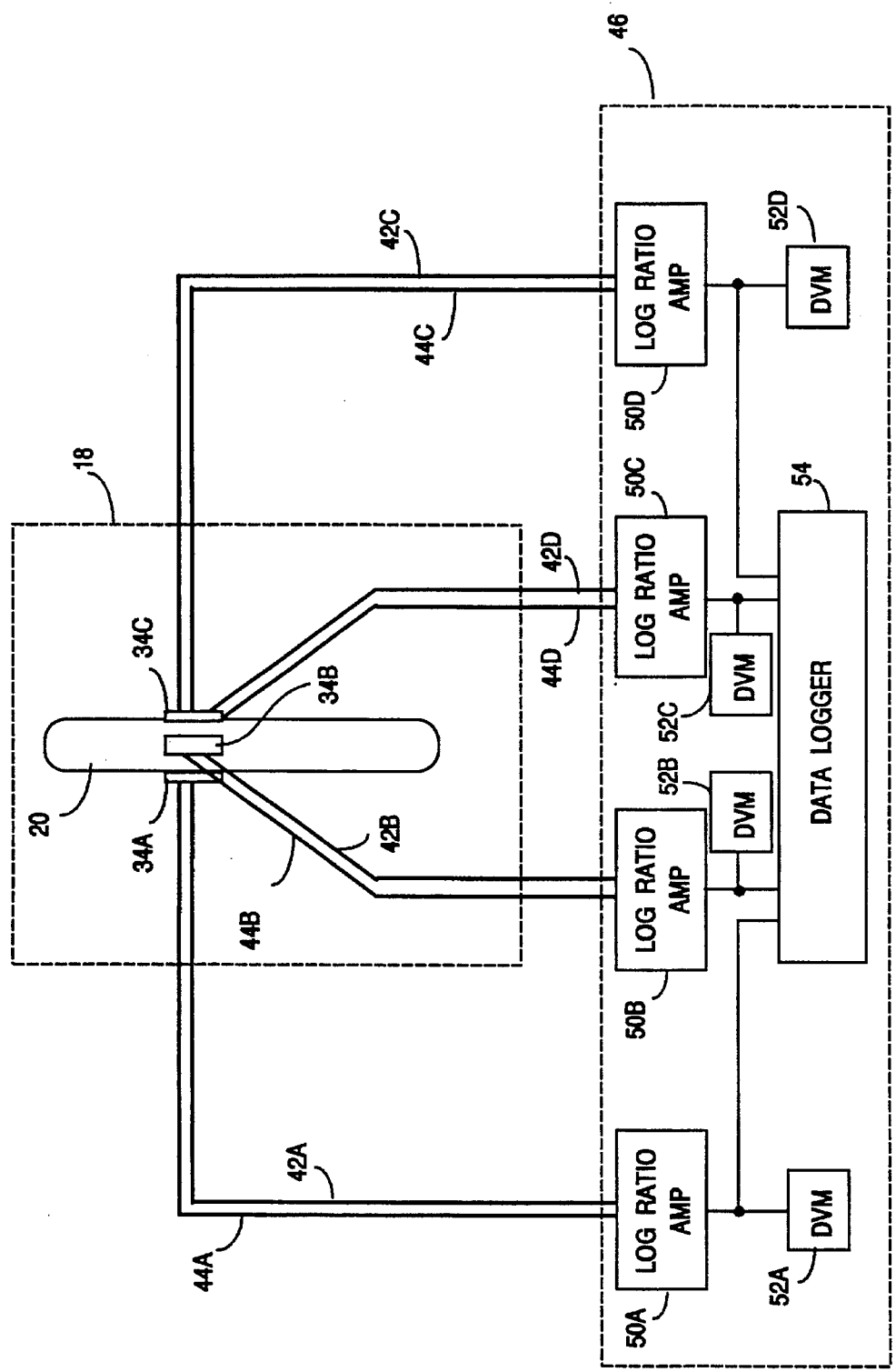
FIG. 3 is a block diagram of the instrumentation used with the present invention.

FIG. 3 is a block diagram showing instrumentation, according to a preferred embodiment of the present invention. IGA/SCC associated with the crevice region of tube 20 is monitored with strain gages 34A, 34B, 34C, 34D. Because longterm monitoring at temperatures typically exceeding perhaps 500° F. is desired, these gages are preferably microbend fiber optic units, such as depicted in FIG. 2. Conventional strain gages simply do not tend to function at such temperatures on a longterm basis.

Each gage receives input light on lead 42A from a source 42 within a log ratio amplifier, e.g., 50A, associated with instrumentation 46. This light is modulated as it passes through fiber optic 37 (see FIG. 2) within strain gage 34A, by force associated by the tooth blocks 38A, 48B. The modulated light output is coupled on lead 44A to the same log ratio amplifier where the light energy is converted to a signal voltage. Log ratio amplifiers are known in the art, and in combination with photodiode detectors, perform an optical-to-electronic signal conversion.

As shown in FIG. 3, a conventional digital volt meter (e.g., 52A) may be coupled to measure the output from each log ratio amplifier, for example, a Hewlett Packard model HP 34401A meter. All of the output voltages from the log ratio amplifiers are coupled as input to a data logger 54, for example Molytek model 3702-5H. The data logger records and prints a graph-like record of output data.

Figure 4:
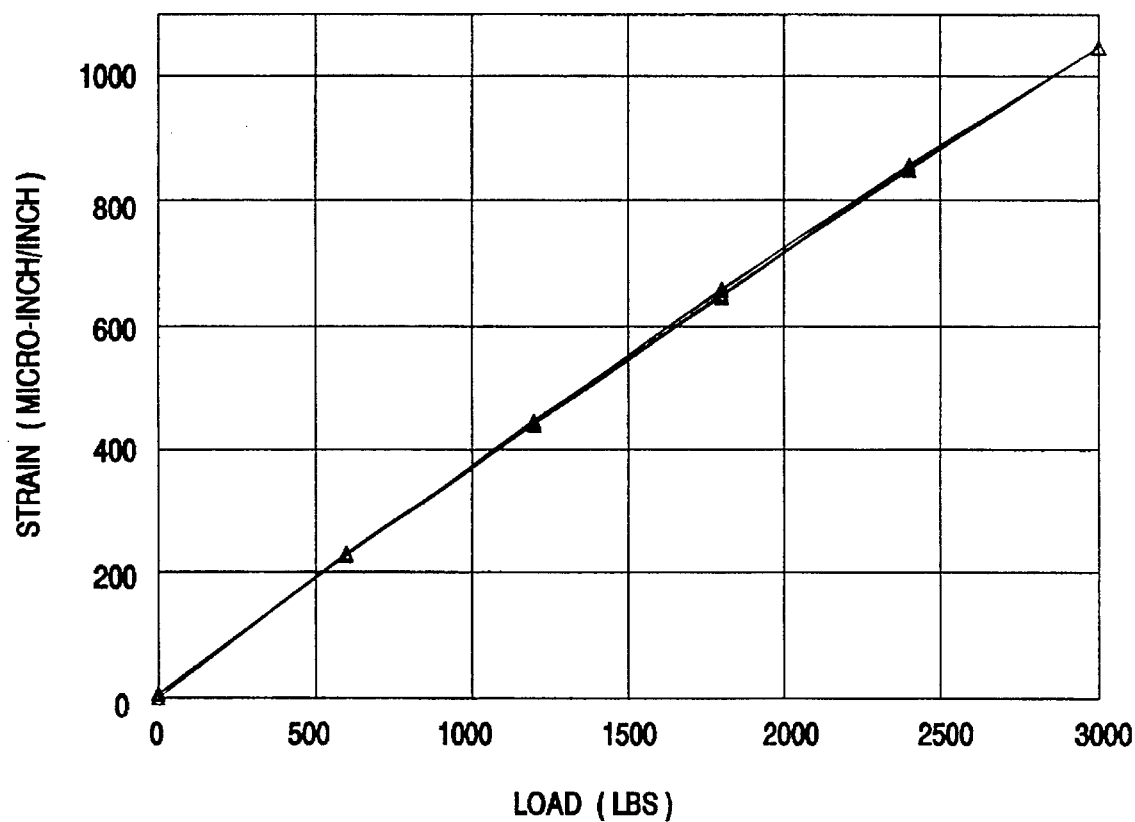
FIG. 4 is a plot of data obtained from pipe 20 from one microbend fiber optic strain gage.

FIG. 4 depicts calibration data obtained from an Inconel alloy 600 tube 20, using a microbend fiber optic strain gage. As shown, the data are linear. Axial loading was applied up to 3000 pounds (1,354 kg). During this test operation, the load was set at 615 pounds (280 kg). For a fixed axial loading of 615 pounds (280 kg), the measured strain (as read on the y-axis of FIG. 4) would increase with progressive IGA/SCC, until ultimately failure of the thin wall occurs.

To aggravate the corrosion process during the testing, a 10% solution of sodium hydroxide, NaOH (attacking fluid) was circulated through pipes 14 and 20 at about 550° F.

Those skilled in the art will appreciate that many other techniques may be used to simulate the corrosive effects of actual water chemistry. An especially adverse pH condition may be established within tube 20, or tube 20 may be fabricated from a material more prone to IGA/SCC effects than the actual pipes within plant 16, and so forth.

Figure 5:
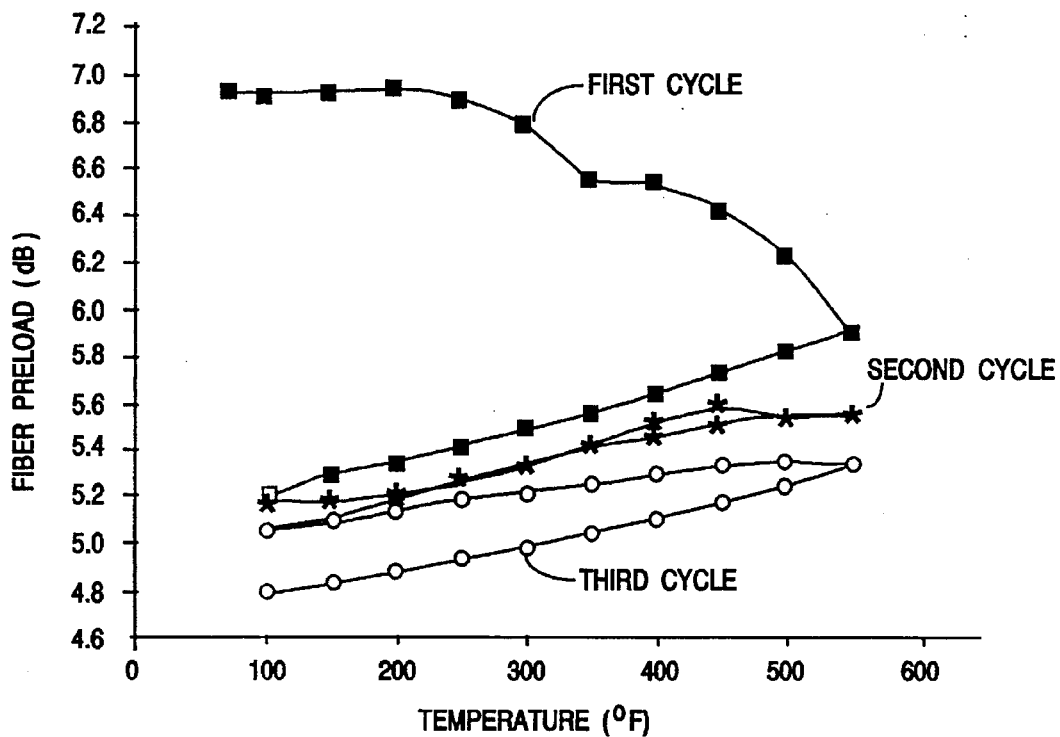
FIG. 5 is a plot of preload loss as a function of temperature, according to the present invention.

As noted from FIG. 2, the outer surface of fiber optic 37 is clamped between tooth blocks 38A, 38B. Those skilled in the art will appreciate that fiber optic 37 includes a core, a clad, and an outer buffer layer. When tooth blocks 38A, 38B first exert force against the buffer layer, the buffer layer begins to crush. FIG. 5 represents a "shake-down" operation to stabilize the output as a function of temperature, at constant preload (strain) of strain gage 34B. As shown therein, during a first cycle of thermal heat-up and cool-down, there is substantial change in the fiber preload as a function of temperature. But after three cycles, there is substantial repeatability in the thermal response of the strain gage output, e.g., preload versus temperature. It will be noted that FIG. 5 (as well as FIGS. 6, 7 and 8) has an axis designated in dB. This axis represents light transmission for a given tooth block displacement corresponding to a given mechanical load on the tooth blocks and optical fiber comprising the strain gage.

Figure 6:
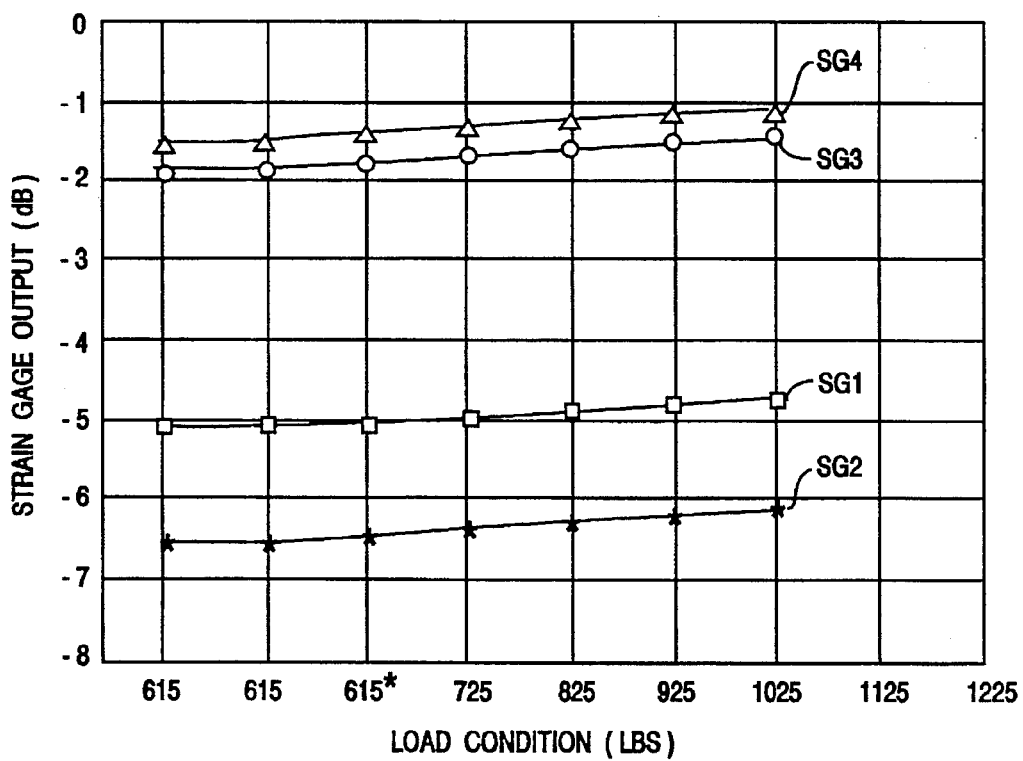
FIG. 6 is a plot of strain gage output as a function of applied load, according to the present invention.

FIG. 6 depicts the output from four fiber optic strain gages (denoted SG1–SG4) as a function of load condition, after about 350 hours of testing. The linear data shown reflect the fact that the strain gages were suitably thermally "shaken down" as has been described with respect to FIG. 5. The slopes of the curves shown in FIG. 6 are substantially the same, although the initial preload value for each strain gage fiber may differ following the thermal shake down. For example, strain gage 4 had a preload of about –1.5 dB, whereas strain gage 2 had a preload of about –6.5 dB.

In FIG. 6, it is to be noted that the first two load condition data points for 615 pounds represents 1,100 psi pressure within tube 20. Thus, the slope between these two points is essentially zero. By contrast, the third data point for 615 lbs (noted as 615*) includes the axial stress resulting when tube 20 was internally pressurized to 1,700 psi as were all other data points to the right of 615*. As a result, there is a slight increase in the strain gage output slope.

Figure 7:
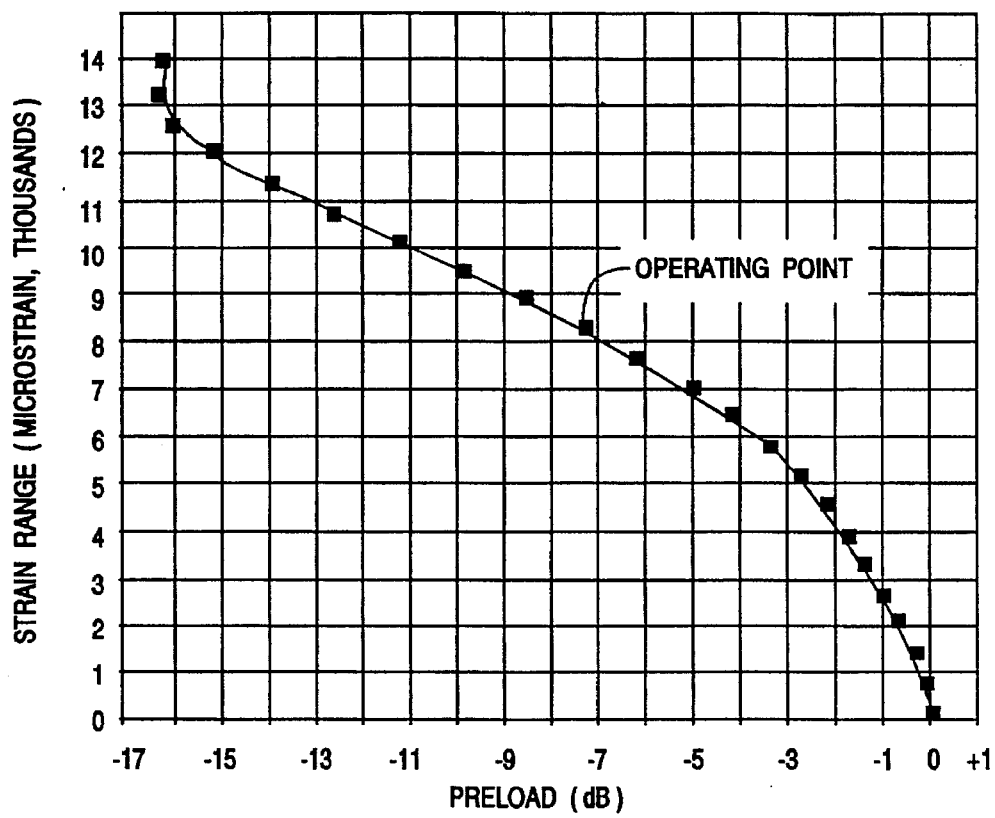
FIG. 7 is a plot of strain gage range as a function of preload, according to the present invention.

Turning now to FIG. 7, a calibration characteristic for strain gage two (SG2) is shown as a function of preload. The nominal operating point was about –7 dB with no axial load applied to tube 20. It will be appreciated that the operating point is chosen to be in the linear range of FIG. 7. Preload is selected for a given strain gage by slightly moving tooth blocks, e.g., 38A, 38B, prior to spot welding the blocks to the outer surface of tube 20.

Figure 8:
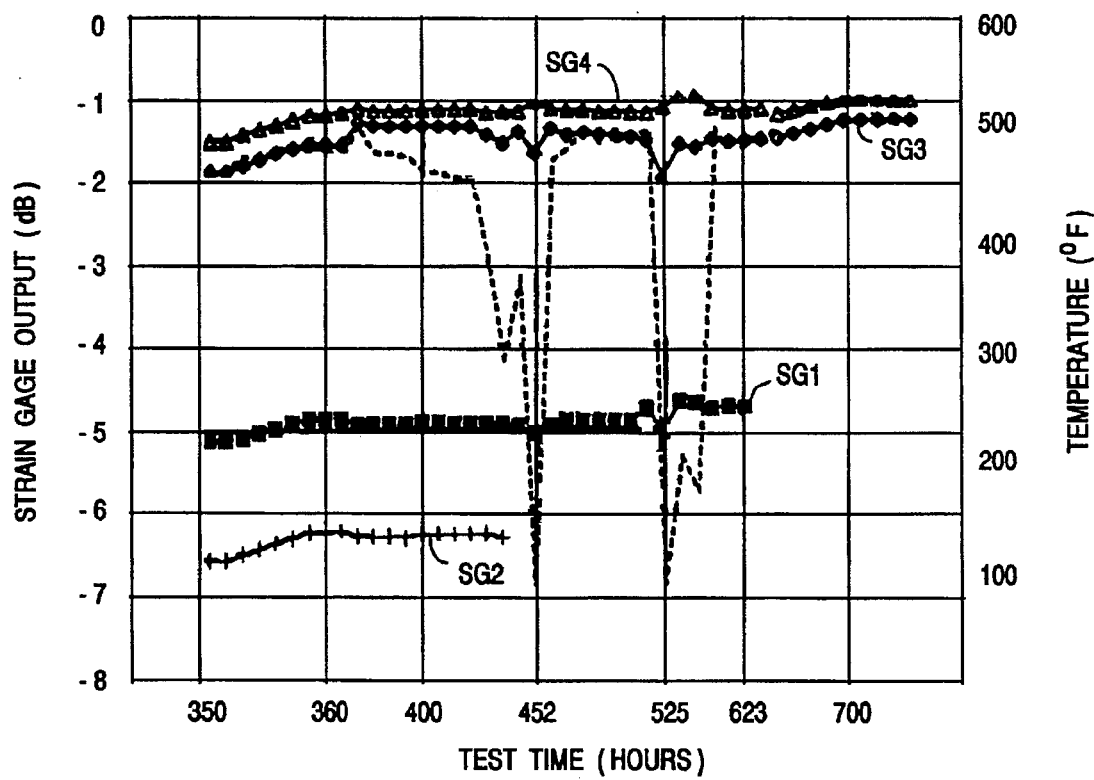
FIG. 8 is a plot of strain gage outputs as a function of time, according to the present invention.

FIG. 8 depicts strain gage output for the four strain gages under test as a function of testing time and temperature. It may be useful at this juncture to compare FIG. 6 and FIG. 8, noting that the horizontal axis of FIG. 8 is not linear. At approximately 350 hours of testing, the output of each strain gage as shown in FIG. 8 was approximately the same as the outputs shown in FIG. 6. The increase in strain with load that is shown in FIG. 6 is the same increase in strain with load shown in FIG. 8 between hours 350 and 360. In FIG. 8, for data beyond hour 360 up to about hour 625, a constant axial load (1,025 pounds) and an increased constant internal tube 20 pressure (about 1,700 psi) were used.

It is seen in FIG. 8 that the data are substantially constant despite variations in fluid temperature. In general, temperature variations resulted from the inability of the system to maintain a constant fluid temperature, temperature being shown in FIG. 8 by the dashed lines.

FIG. 8 shows only two regimes of systematic changes in strain, apart from the obvious constant strain as a function of time. More specifically, the first regime occurs between 350 hours and 360 hours, during which time the axial load was systematically increased from 615 pounds to 1,025 pounds. The second regime occurs between 625 hours and 700 hours, during which time the axial load was systematically increased from 1,025 pounds to about 1,200 pounds.

It must be noted that an unplanned shutdown (e.g., cool down) of the test section occurred at about 450 hours due to leaks in the fittings connecting tube 20 to the pump (not shown) that circulated the 10% solution of NaOH. Note that even though the temperature now changed drastically, the strain gage outputs changed but a few tenths of a dB. Similarly, after the leakage problem was attended to and elevated temperature was restored, the outputs of strain gage 1, 3 and 4 returned to their previous values. A second leak also occurred at about hour 515, which required a second shutdown of the test system. No data appears for strain gate SG2 beyond about 440 hours, and for strain gage SG1 beyond about 623 hours due to unplanned breakage in the optical leads coupling the strain gages to the associated log ratio amplifier.

Between about 650 hours and 700 hours, the axial load on tube 20 was incrementally increased from 615 pounds to about 1,200 pounds (909 kg) to try to accelerate the time necessary to cause tube failure. Note that the outputs of the remaining strain gages SG3, SG4 increase slightly, and successfully track the resultant increase in strain resulting from the change in axial load. Unfortunately the test had to be concluded at about 750 hours before tube 20 fractured.

Subsequent destructive examination of tube 20 revealed that wall thinning due to IGA/SCC occurred. However the location was in region 36 in FIG. 1, rather than in region 24 as was expected. Region 36 was a notch where the outside surface of heater 26 contacted the inside surface of tube 20 at the beginning of the taper that defined crevice 24. A gouge of depth 0.013" was discovered in that notch. However, the resultant wall thinning due to IGA/SCC was not less than 0.030", which was the dimension of the intentionally thinned wall section. For this reason, observable changes in strain during the 750 hour test attributable to IGA/SCC were not readily apparent.

However had the test been allowed to continue for an additional few hundred hours, IGA/SCC would have continued to progress and the resultant gouge would have deepened until the wall thinned to less than 0,030". Under these conditions, the increase in strain would have been readily detectable, as indicated by FIG. 6, in which the gages continue to track increasing strain. As noted with respect to FIG. 1, in future embodiments, it is anticipated that at least some strain gages will be located adjacent the notch region 36, which locations are shown in phantom.

During the approximately 750 hours of experimentation reflected in FIG. 8, the repeatability of the strain gages used was determined to be about ±30 microstrain. Given the fact that prior art configurations and strain gages would not likely have survived the entire time period of applicants test, it is apparent that the present invention can be used to predict onset and progression of IGA/SCC.

Modifications and variations may be made to the disclosed embodiments without departing from the subject and spirit of the invention as defined by the following claims.

What is claimed is:

1. A method for predicting onset of intergranular attack, stress corrosion cracking, or both in tubing associated with a power generator plant, the method comprising the following steps:

(a) providing a tube in fluid communication with said tubing, said tube having an internal pressure commensurate with said tubing, and having a crevice region;

(b) providing at least one optical strain gage on an external surface of said tube at a location corresponding to a general location of said crevice region; and (c) monitoring said at least one optical strain gage to determine strain in said tube, said strain being used to predict onset of intergranular attack, stress corrosion cracking, or both in said tubing.

2. The method of claim 1, including an additional step of subjecting said tube to controlled axial loading.

3. The method of claim 1, wherein a region of said tube adjacent said crevice region has a thinned wall.

4. The method of claim 1, further including a step of providing a heater within said tube, said heater further promoting a water starved region in said crevice region.

5. The method of claim 1, wherein said at least one optical strain gage is a microbend fiber optic strain gage.

6. The method of claim 1, wherein said tube is made of a material substantially identical to material from which at least some of said tubing is made.

7. The method of claim 1, wherein said tube is made of a material more subject to corrosion than is material from which at least some of said tubing is made.

8. The method of claim 1, wherein fluid within said tube is caused to be more corrosive than fluid within at least some of said tubing by taking at least one measure selected from the group consisting of (i) altering pH within said tubing, and (ii) adding corrosion-promoting substances to fluid within said tubing.

9. The method of claim 1, further including the step of surrounding said tube with an autoclave.

10. The method of claim 1, wherein said tube has at least one dimension selected from the group consisting of (i) an outer diameter of about 0.75" (1.905 cm), (ii) a nominal wall thickness of about 0.04" (1 mm), (iii) a length of about 6" (15.24 cm), and (iv) a thin walled thickness of about 0.03" (0.76 mm).

11. A system for predicting onset of intergranular attack, stress corrosion cracking, or both in tubing associated with a power generator plant, the system comprising:

a tube in fluid communication with said tubing, said tube having an internal pressure commensurate with said tubing, and having a crevice region;

at least one optical strain gage, disposed on an external surface of said tube at a location corresponding to a general location of said crevice region;

wherein strain in said tube is detected by said at least one optical strain gage, said strain being used to predict onset of intergranular attack, stress corrosion cracking, or both in said tubing.

12. The system of claim 11, further including an axial load, controllably coupled to an end of said tube to provide a chosen one of a loaded condition and an unloaded condition.

13. The system of claim 11, wherein a region of said tube adjacent said crevice region has a thinned wall.

14. The system of claim 11, further including a heater disposed within said tube, said heater further promoting a water starved region in said crevice region.

15. The system of claim 11, wherein said at least one optical strain gage is a microbend fiber optic strain gage.

16. The system of claim 11, wherein said tube is made of a material substantially identical to material from which at least some of said tubing is made.

17. The system of claim 11, wherein said tube is made of a material more subject to corrosion than is material from which at least some of said tubing is made.

18. The system of claim 11, wherein fluid within said tube is caused to be more corrosive than fluid within at least some of said tubing by taking at least one measure selected from the group consisting of (i) altering pH within said tubing, and (ii) adding corrosion-promoting substances to fluid within said tubing.

19. The system of claim 11, further including an autoclave surrounding said tube.

20. The system of claim 11, wherein said crevice region is formed by (i) inserting a radially-inward projecting member from an inner surface of said pipe, (ii) filling said crevice region with a porous plug containing corrosion product material, or a combination of (i) and (ii).

* * * * *